United States Patent [19]

Boll

[11] Patent Number: Plant 5,390

[45] Date of Patent: Jan. 15, 1985

[54] BEGONIA PLANT NAMED PIA ELISE

[75] Inventor: Holger Boll, Odense, Denmark

[73] Assignee: L. Daehnfeldt Ltd., Odense, Denmark

[21] Appl. No.: 506,212

[22] Filed: Jun. 20, 1983

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

A new and distinct cultivar of begonia named Pia Elise, comprising a flower color mutation of the cultivar Barbara, and particularly characterized by its large double, deep pink flowers which do not significantly fade under abnormal conditions, with the flower color pleasantly contrasting with dark green foliage, vigorous growth habit, and by its ease of manipulation for year around flower production, especially for larger containers and hanging baskets for interior decorating.

1 Drawing Figure

The present invention relates to a new and distinct cultivar of begonia plant, botanically known as *Begonia hiemalis* (Fotsch) and known by the cultivar name Pia Elise.

The new cultivar was discovered by me in Odense, Denmark as a color mutation of the cultivar Barbara, disclosed in Application Ser. No. 420,498 of Erland V. Schelbeck, filed Sept. 20, 1982; Pia Elise was observed in a group of flowering plants of Barbara in 10 cm. pots in a controlled environment in Odense, Denmark.

Asexual reproduction by me in Odense, Denmark by stem and/or leaf cuttings has reproduced the unique features of the new cultivar through successive propagations.

The following characteristics distinguish Pia Elise from both its parent cultivar Barbara and other begonias commercially known and used in the floriculture industry:

1. In comparison to Barbara, which has a flower color of red purple 73B, the flower color of Pia Elise is red 52A-B with basal tepals 52A, with the underside of of tepals being red 55A.

2. The flowers of Pia Elise are slightly less double than those of Barbara and are somewhat larger in diameter.

3. In all other respects the mutation has nearly the same morphological appearance as the parent excepting slightly darker foliage.

4. The new cultivar is considered to be highly floriferous. The stems on which flowering occurs tend to have initiation and development at several nodes at one time.

5. The keeping qualities of the flowers and the foliage in all seasons allows production and sales efficiencies to be maximized.

6. The new cultivar tends to be very vigorous so that 10 cm. pot production is best done with shoot cuttings and tip pinching.

7. Propagation by leaf cuttings is difficult under light and high temperatures in summer months. Stem cuttings can readily be produced in this season.

8. The flowers of Pia Elise undergo little or no fading under abnormal conditions, which, together with its excellent keeping qualities, make it especially suitable for hanging baskets.

The accompanying colored photograph taken April 1983 illustrates in perspective the overall appearance of Pia Elise grown in a 12 cm. pot from a leaf cutting, and shows the colors as true as it is reasonably possible to obtain in a colored reproduction of this type.

The following is a detailed description of my new begonia cultivar based on plants produced under commercial practices in glasshouses in Odense, Denmark and Ashtabula, Ohio. Color references are made to The Royal Horticultural Society Colour Chart except where general color terms of ordinary dictionary significance are used.

PARENTAGE

A mutation of the cultivar Barbara.

PROPAGATION

Type cutting: Stem cutting.

Time to root for planting: 27–30 Days at 21° C. summer; 25–28 days at 21° C. winter.

Rooting habit: Uniform, dendritic, fibrous,

Time for shoot development of leaf cutting: 70–85 Days to develop adventitious shoots 5–6 cm. long from stick date.

PLANT DESCRIPTION

Form: Low bush type, self branching, herbaceous.

Habit of growth: Generally rapid, vigorous with strong stems, strong peduncles, and strong pedicels.

Foliage: Leaves simple, alternate; borne on vigorous petioles; firm.

(1) *Size.*—Average leaf at maturity from 10–12 cm. long. Leaves may be larger or smaller depending on density of leaf canopy.

(2) *Shape.*—Ovate, slightly concave.

(3) *Texture.*—Leaf is firm, top glabrous, underside rugose.

(4) *Margin.*—Crenate.

(5) *Color.*—Young foliage top side, green 137D, underside, yellow green 146D; mature foliage top side darker than yellow green 147A; under side yellow green 147B to 148A.

(6) *Venation.*—Palmate.

FLOWERING DESCRIPTION

Flowering habits: Flowering in racemes, with several clusters arising from the stem nodes at same time giving a highly floriferous appearance. Flowering is continuous for long periods of time.

Natural flowering season: Flowering occurs naturally with shortened day lengths beginning mid-September and continuing through May. Reducing day length in summer speeds up flower initiation.

Flower bud description: Flat, round, very light pink, progressively deepening in color until tepals begin to open.

Flowers borne: On vigorous peduncles and pedicels in a raceme. The extra doubleness of the flowers causes a pendulous appearance because of the weight of the flowers.

0 Quantity: Very floriferous, often having 18–20 flowers per main stem in flowering stage at one time.

Tepals:

(1) *Shape.*—Nearly circular.

(2) *Color.*—Top side in winter when opening at 16° C., red 52A; color when fully open has brighter tone than red 52BC; color remains uniform relative to temperature regime; under side red 55A.

(3) *Number of tepals.*—From 14 to 26.

(4) *Size of tepals.*—4 basal tepals 25–30 mm., interior tepals 10–20 mm.

(5) *Flower size.*—From 5–7 cm.

Reproductive organs: None — sterile triploid.

DISEASE RESISTANCE

No particular increase in resistance to diseases observed to date.

I claim:

1. A new and distinct cultivar of begonia named Pia Elise, as illustrated and described, comprising a flower color mutation of the cultivar Barbara, and particularly characterized by its large double, deep pink flowers which do not significantly fade under abnormal conditions, with the flower color pleasantly contrasting with dark green foliage; vigorous growth habit, and by its ease of manipulation for year around flower production, especially for larger containers and hanging baskets for interior decorating.

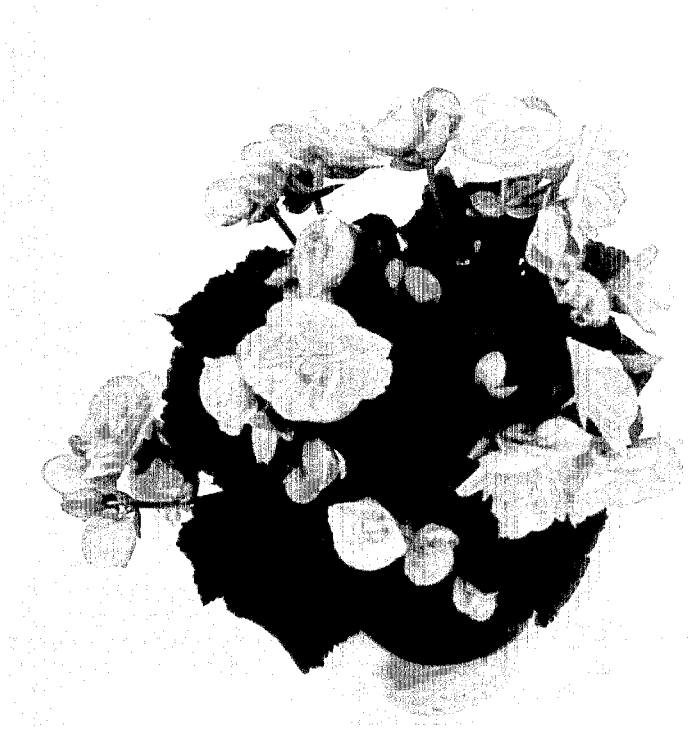

* * * * *